US012747460B2

(12) United States Patent
Hong et al.

(10) Patent No.: US 12,747,460 B2
(45) Date of Patent: Sep. 29, 2026

(54) KETOREDUCTASE MUTANT AND METHOD FOR PRODUCING CHIRAL ALCOHOL

(71) Applicant: ASYMCHEM LABORATORIES (FUXIN) CO., LTD., Fuxin (CN)

(72) Inventors: Hao Hong, Morrisville, NC (US); Gage James, Morrisville, NC (US); Yi Xiao, Tianjin (CN); Na Zhang, Tianjin (CN); Xuecheng Jiao, Tianjin (CN); Kejian Zhang, Tianjin (CN); Yiming Yang, Tianjin (CN); Xiang Wang, Tianjin (CN); Yanqing Zhang, Tianjin (CN)

(73) Assignee: ASYMCHEM LABORATORIES (FUXIN) CO., LTD., Fuxin (CN)

( * ) Notice: Subject to any disclaimer, the term of this patent is extended or adjusted under 35 U.S.C. 154(b) by 1111 days.

(21) Appl. No.: 17/774,891

(22) PCT Filed: Nov. 7, 2019

(86) PCT No.: PCT/CN2019/116360
§ 371 (c)(1),
(2) Date: May 6, 2022

(87) PCT Pub. No.: WO2021/087894
PCT Pub. Date: May 14, 2021

(65) Prior Publication Data

US 2022/0403421 A1 Dec. 22, 2022

(51) Int. Cl.

| | |
|---|---|
| ***C12P 7/24*** | (2006.01) |
| ***C12N 1/20*** | (2026.01) |
| ***C12N 9/04*** | (2006.01) |
| ***C12N 15/70*** | (2006.01) |

(52) U.S. Cl.
CPC .................. *C12P 7/24* (2013.01); *C12N 1/20* (2013.01); *C12N 9/0006* (2013.01); *C12N 15/70* (2013.01); *C12Y 101/01184* (2013.01); *C12N 2800/101* (2013.01)

(58) Field of Classification Search
CPC ........... C12P 7/24; C12N 1/20; C12N 9/0006; C12N 15/70; C12Y 101/01184
See application file for complete search history.

(56) References Cited

U.S. PATENT DOCUMENTS

2009/0311762 A1* 12/2009 Tschentscher ............ C12P 7/02 435/135

FOREIGN PATENT DOCUMENTS

| | | |
|---|---|---|
| CN | 108048417 A | 5/2018 |
| CN | 110257351 | 9/2019 |
| CN | 110713992 | 1/2020 |
| WO | 2019140682 A1 | 7/2019 |

OTHER PUBLICATIONS

Filling et al., "Critical Residues for Structure and Catalysis in Short-chain Dehydrogenases/Reductases", 2002, Journal of Biological Chemistry, pp. 25677-25684 (Year: 2002).*
Wei et al., "Significantly enhancing the biocatalytic synthesis of chiral alcohols by semi-rationally engineering an anti-Prelog carbonyl reductase from *Acetobacter* sp. CCTCC M209061", 2019, Molecular Catalysis, pp. 1-8. (Year: 2019).*
1HXH_D, "Comamonas testosteroni ATCC 11996 3β/17β-HSD SDR family oxidoreductase", https://www.ncbi.nlm.nih.gov/protein/1HXH_D (Year: 2023).*
WP_062810033.1, "Glucose 1-dehydrogenase [*Novacetimonas hansenii*]", https://www.ncbi.nlm.nih.gov/protein/WP_062810033.1 (Year: 2019).*
GenBank: MBL7237875.1, "Glucose 1-dehydrogenase [*Novacetimonas hansenii*]", https://www.ncbi.nlm.nih.gov/protein/MBL7237875.1/, (Year: 2021).*
Japanese Office Action in Application No. 2022-527053, Issued Mar. 29, 2024, 2 Pages.
Supplementary European Search Report for EP 19951528, Issued Oct. 24, 2022, 5 Pages.
Zoller, M. J., et al., "Oligonucleotide-directed mutagenesis using M13-derived vectors: an efficient and general procedure for the production of point mutations in any fragment of DNA," Nucleic Acids Research, vol. 10, No. 20 (1982), pp. 6487-6500.

* cited by examiner

*Primary Examiner* — Thomas J. Visone
(74) *Attorney, Agent, or Firm* — Riverside Law LLP

(57) ABSTRACT

Disclosed are a ketoreductase mutant and a method for producing a chiral alcohol. The ketoreductase mutant has an amino acid sequence obtained by the mutation of the amino acid sequence shown in SEQ ID NO: 1, and the mutation includes a mutation siteK200H.

20 Claims, No Drawings

Specification includes a Sequence Listing.

KETOREDUCTASE MUTANT AND METHOD FOR PRODUCING CHIRAL ALCOHOL

CROSS-REFERENE TO RELATED APPLICATIONS

This application is a U.S. National Phase Application filed under 35 U.S.C. § 371 claiming benefit to International Patent Application No. PCT/CN2019/116360, which was filed on Nov. 7, 2019, the entire contents of which are incorporated by reference in its entirety.

SEQUENCE LISTING

The present application contains a Sequence Listing which has been submitted electronically in ASCII format and is hereby incorporated by reference in its entirety. Said ASCII copy is named PN173504_Sequence_List_JTY_20220429.txt and is 2,467.84 bytes in size, and contains 1 sequence SEQ ID NO:1, which is identical to the sequence listing filed in the corresponding international application No. PCT/CN2019/116360 filed on Nov. 7, 2019.

TECHNICAL FIELD

The present disclosure relates to the technical field of compound synthesis, in particular to a ketoreductase mutant and a method for producing a chiral alcohol.

BACKGROUND

Chiral alcohol widely exists in the natural world, is a structural unit of many important biologically active molecules, and is an important intermediate for synthesis of natural products and chiral drugs. Many chiral drugs contain one or more chiral centers. The pharmacological activities, metabolic processes, metabolic rates, and toxicities of the different chiral drugs are significantly different. Usually one enantiomer is effective, and the other enantiomer is ineffective or non-effective, or even toxic. Therefore, how to efficiently and stereoselectively construct a compound containing the chiral center is of great significance in pharmaceutical research and development.

Ketoreductase (KRED) may also be called Carbonyl-reductase, the enzyme classification number is EC 1.1.1.184, and is often used to reduce latent chiral aldehydes or ketones to prepare the chiral alcohol. KRED may not only convert aldehyde or ketone substrates into corresponding alcohol products, but also catalyze its reverse reaction, namely catalyze the oxidation of alcohol substrates to obtain the corresponding aldehydes or ketones. In a reaction catalyzed by the ketoreductase, the participation of cofactors is required, including reduced nicotinamide adenine dinucleotide (NADH), reduced nicotinamide adenine dinucleotide phosphate (NADPH), oxidized nicotinamide adenine dinucleotide ($NAD^+$) or oxidized nicotinamide adenine dinucleotide phosphate ($NADP^+$).

In the reduction reaction process of the aldehydes or ketones, the reduced cofactor NADH or NADPH is generally required. In the actual reaction, the oxidized cofactor $NAD^+$ or $NADP^+$ may be added, and then regenerated into the reduced NADH or NADPH by a suitable cofactor regeneration system. The commonly used cofactor regeneration system includes glucose and glucose dehydrogenase, formate and formate dehydrogenase, secondary alcohol and secondary alcohol dehydrogenase, phosphite and phosphite dehydrogenase, and other similar systems. In general, the replacement of the coenzyme regeneration system may not substantially affect the function of the ketoreductase.

Although a variety of KREDs are already used in commercial production, KRED generally has the disadvantage of low stability in application, it is specifically embodied in thermal stability and resistance to organic solvents. Enzyme modification by means of directed evolution may improve the stability of an enzyme, so it may be better applied in production.

SUMMARY

The present disclosure aims to provide a ketoreductase mutant and a method for producing a chiral alcohol, as to improve the stability of a ketoreductase.

In order to achieve the above purpose, according to one aspect of the present disclosure, a ketoreductase mutant is provided. The ketoreductase mutant has an amino acid sequence obtained by the mutation of the amino acid sequence shown in SEQ ID NO: 1, and the mutation includes a mutation site K200H.

Further, the mutation includes at least one of the following mutation sites: A15, K28, G36, K39, G43, Q44, A46, V47, F59, K61, T65, K71, A94V, A144, M146, Y152, N156, I86, K208 or K237; or the amino acid sequence of the ketoreductase mutant is an amino acid sequence having the mutation site in a mutated amino acid sequence, and having more than 95% identity with the mutated amino acid sequence.

Further, the mutation include at least one of the following mutation sites: A15C, K28A/E/M/Q/R/S, G36C, K39I/V, G43C/M, Q44R, A46C, V47C, F59C, K61E/H, T65A, K71R, A94V, A144T, M146I, Y152F, N156S, I86V, K208R or K237E.

Further, the mutation includes any one of the following mutation site combinations: Q44R+N156S+K200H, Q44R+N156S+K200H+G201D, Q44R+N156S+K200H+G201D+M146I, Q44R+N156S+K200H+G201D+M146I+K61H, Q44R+N156S+K200H+G201D+M146I+K61H+I86V, Q44R+N156S+K200H+G201D+M146I+K61H+K208R, Q44R+N156S+K200H+G201D+M146I+K61H+K208R+A94V, Q44R+N156S+K200H+G201D+M146I+K61H+K208R+A94V+K39I+A15C, Q44R+N156S+K200H+G201D+M146I+K61H+K208R+A94V+K39I+A15C+A46C, Q44R+N156S+K200H+G201D+M146I+K61H+K208R+A94V+K39I, or Q44R+N156S+K200H+G201D+M146I+K61H+K208R+A94V+K39I+A15C+A46C+G43M.

Further, the occurrence of the amino acid mutation includes any one of the following mutation site combinations: I86V+M146I+K200H, M146I+K200H, M146L+N156S+K200H, M146L+K200H, K200H+G201D, Q44R+M146I+K200H, K61E+K200H+K237E, I86V+M146I+K200H, M146I+K200H+G201D, M146L+K200H+G201 D, N156S+K200H+G201D, K200H+G201D+K237E, K28E+M146I+K200H+G201D, K28E+M146L+K200H+G201D, K28E+N156S+K200H+G201D, Q44R+M146L+K200H+G201D, Q44R+N156S+K200H+G201D, I86V+M146I+K200H+K61H, 186V+M146I+K200H+K208R, I86V+M146I+K200H+G201 D, I86V+M146L+K200H+G201 D, Q44R+N156S+K200H+G201D, Q44R+N156S+K200H+G201 D+M146I, Q44R+N156S+K200H+G201D+M146I+K61H, Q44R+N156S+K200H+G201D+M146I+K61H+K28E, Q44R+N156S+K200H+G201D+M146I+K61H+T65A, Q44R+N156S+K200H+G201D+M146I+K61H+I86V, Q44R+N156S+K200H+G201D+M146I+K61H+K208R, Q44R+N156S+K200H+G201D+M146I+K61H+

I86V+K28E, Q44R+N156S+K200H+G201D+M146I+K61H+I86V+K39I, Q44R+N156S+K200H+G201D+M146I+K61H+I86V+T65A, Q44R+N156S+K200H+G201D+M146I+K61H+I86V+A94V, Q44R+N156S+K200H+G201D+M146I+K61H+I86V+K208R, Q44R+N156S+K200H+G201D+M146I+K61H+K208R+K28E, Q44R+N156S+K200H+G201D+M146I+K61H+K208R+K39I, Q44R+N156S+K200H+G201D+M146I+K61H+K208R+A94V, Q44R+N156S+K200H+G201D+M146I+K61H+K208R+A94V+K28E, Q44R+N156S+K200H+G201D+M146I+K61H+K208R+A94V+K39I, Q44R+N156S+K200H+G201D+M146I+K61H+K208R+A94V+T65A. Q44R+N156S+K200H+G201D+M146I+K61H+K208R+A94V+K39I+K28E. Q44R+N156S+K200H+G201D+M146I+K61H+K208R+A94V+K39I, Q44R+N156S+K200H+G201D+M146I+K61H+K208R+A94V+K39I+A15C+A46C, Q44R+N156S+K200H+G201D+M146I+K61H+K208R+A94V+K39I+V47C+F59C, Q44R+N156S+K200H+G201D+M146I+K61H+K208R+A94V+K39I+G43C, Q44R+N156S+K200H+G201D+M146I+K61H+K208R+A94V+K39I+A15C+A46C+K28E, Q44R+N156S+K200H+G201D+M146I+K61H+K208R+A94V+K39I+A15C+A46C+K28R, Q44R+N156S+K200H+G201D+M146I+K61H+K208R+A94V+K39I+A15C+A46C+K28Q, Q44R+N156S+K200H+G201D+M146I+K61H+K208R+A94V+K39I+A15C+A46C+K28M, Q44R+N156S+K200H+G201D+M146I+K61H+K208R+A94V+K39I+A15C+A46C+K28A, Q44R+N156S+K200H+G201D+M146I+K61H+K208R+A94V+K39I+A15C+A46C+K28S, Q44R+N156S+K200H+G201D+M146I+K61H+K208R+A94V+K39I+A15C+A46C+G43M, Q44R+N156S+K200H+G201D+M146I+K61H+K208R+A94V+K39I+A15C+A46C+I86V, Q44R+N156S+K200H+G201D+M146I+K61H+K208R+A94V+K39I+A15C+A46C+G43M, Q44R+N156S+K200H+G201D+M146I+K61H+K208R+A94V+K39I+A15C+A46C+G43M+G36C, Q44R+N156S+K200H+G201D+M146I+K61H+K208R+A94V+K39I+A15C+A46C+G43M+139V, Q44R+N156S+K200H+G201D+M146I+K61H+K208R+A94V+K39I+A15C+A46C+G43M+K71R, Q44R+N156S+K200H+G201D+M146I+K61H+K208R+A94V+K39I+A15C+A46C+G43M+A144T, Q44R+N156S+K200H+G201D+M146I+K61H+K208R+A94V+K39I+A15C+A46C+G43M+Y152F, Q44R+N156S+K200H+G201D+M146I+K61H+K208R+A94V+K39I+A15C+A46C+G43M+K28E, or Q44R+N156S+K200H+G201D+M146I+K61H+K208R+A94V+K39I+A15C+A46C+G43M+G36C.

According to another aspect of the present disclosure, a deoxyribonucleic acid (DNA) molecule is provided. The DNA molecule encodes the above ketoreductase mutant.

According to another aspect of the present disclosure, a recombinant plasmid is provided. The recombinant plasmid contains the above DNA molecule.

Further, the recombinant plasmid is pET-22a (+) pET-22b (+) pET-3a (+) pET-3d (+), pET-11a (+), pET-12a (+), pET-14b (+), pET-15b (+), pET-16b (+), pET-17b (+), pET-19b (+), pET-20b (+), pET-21a (+), pET-23a (+), pET-23b (+), pET-24a (+), pET-25b (+), pET-26b (+), pET-27b (+), pET-28a (+), pET-29a (+), pET-30a (+), pET-31b (+), pET-32a (+), pET-35b (+), pET-38b (+), pET-39b (+), pET-40b (+), pET-41a (+), pET-41b (+), pET-42a (+), pET-43a (+) pET-43b (+), pET-44a (+), pET-49b (+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

According to another aspect of the present disclosure, a host cell is provided. The host cell contains any one of the above recombinant plasmids.

Further, the host cell includes a prokaryotic cell or a eukaryotic cell; preferably, the prokaryotic cell is *Escherichia coli.*

According to another aspect of the present disclosure, a method for producing a chiral alcohol is provided. The method includes a step of catalyzing a reduction reaction of a latent chiral ketone compound to produce the chiral alcohol by a ketoreductase, and the ketoreductase is any one of the above ketoreductase mutants.

Further, the chiral ketone compound has the following structural formula

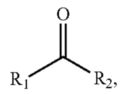

herein $R_1$ and $R_2$ are each independently an alkyl, a cycloalkyl, an aryl or a heteroaryl, or $R_1$ and $R_2$ form a heterocyclyl, a carbocyclyl or a heteroaryl together with carbon in a carbonyl, heteroatom in the heterocyclyl or the heteroaryl is each independently at least one of nitrogen, oxygen or sulfur, an aryl group in the aryl, a heteroaryl group in the heteroaryl, a carbocyclyl group in the carbocyclyl or a heterocyclyl group in the heterocyclyl is each independently unsubstituted or substituted with at least one of a halogen, an alkoxy, or an alkyl.

$R_1$ and $R_2$ are each independently a $C_1$-$C_8$ alkyl, a $C_5$-$C_{10}$ cycloalkyl, a $C_5$-$C_{10}$ aryl or a $C_5$-$C_{10}$ heteroaryl, or $R_1$ and $R_2$ form a $C_5$-$C_{10}$ heterocyclyl, a $C_5$-$C_{10}$ carbocyclyl or a $C_5$-$C_{10}$ heteroaryl together with carbon in a carbonyl, heteroatoms in the $C_5$-$C_{10}$ heterocyclyl or the $C_5$-$C_{10}$ heteroaryl are each independently at least one of nitrogen, oxygen or sulfur, an aryl group in the $C_5$-$C_{10}$ aryl, a heteroaryl group in the $C_5$-$C_{10}$ heteroaryl, a carbocyclyl group in the $C_5$-$C_{10}$ carbocyclyl or a heterocyclyl group in the $C_5$-$C_{10}$ heterocyclyl is each independently unsubstituted or substituted with at least one of a halogen, an alkoxy, or an alkyl.

Preferably, the structure of the ketone compound is

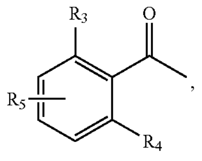

herein, $R_3$ is H, F, Cl, Br or $CH_3$, $R_4$ is H, F, Cl, Br or $CH_3$, and $R_5$ is H, F, Cl, Br, $CH_3$, $OCH_3$ or $CH_2CH_3$.

More preferably, the ketone compound is

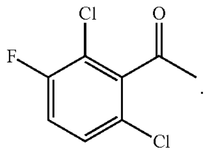

Further, the reaction system for producing the chiral alcohol by reducing the ketone compound with the ketoreductase further includes a coenzyme, a coenzyme regeneration system and a buffer.

Further, the concentration of the ketone compound in the reaction system is 1 g/L-200 g/L.

Further, the pH value of the reaction system is 5-9, and the reaction temperature of the reaction system is 4-60° C.

Further, the coenzyme is NADH.

Further, the coenzyme regeneration system includes: isopropanol, coenzyme $NAD^+$ and ketoreductase.

Further, the buffer is a phosphate buffer, a Tris-hydrochloric acid buffer, a sodium barbital-hydrochloric acid buffer or a citric acid-sodium citrate buffer.

The mutant obtained by the mutation of the present disclosure may use the ketone compound as a raw material, the chiral alcohol may be efficiently produced by stereoselective reduction, and the stability is greatly improved, which is suitable for popularization and application to the industrial production of the chiral alcohol.

DETAILED DESCRIPTION OF THE EMBODIMENTS

It should be noted that embodiments in the present disclosure and features of the embodiments may be combined with each other in the case without conflicting. The present disclosure is described in detail below with reference to the embodiments.

Definitions

"Ketoreductase" and "KRED" are used interchangeably in the present disclosure, and refer to a polypeptide capable of reducing a ketone group into a corresponding alcohol thereof. Specifically, the ketoreductase polypeptide of the present disclosure is capable of stereoselectively reducing a ketone compound into a corresponding alcohol product. The polypeptide usually uses cofactor reduced nicotinamide adenine dinucleotide (NADH) or reduced nicotinamide adenine dinucleotide as a reducing agent. In the present disclosure, the ketoreductase includes a naturally occurring (wild-type) ketoreductase and a non-naturally occurring ketoreductase mutant produced by artificial treatment.

"Naturally occurring" or "wild-type" is opposite to "mutant", and refers to a form found in nature. For example, a naturally occurring or wild-type polypeptide or polynucleotide sequence is a sequence that exists in an organism, it may be isolated from a source in nature, and which has not been intentionally modified by human manipulation.

In the present disclosure, "recombinant" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" refers to comparison between polynucleotides, and is determined by comparing two optimally aligned sequences over a comparison window, herein a portion of a polynucleotide sequence in a comparison window may include addition or deletion (namely, gaps) compared with a reference sequence, which is used for the optimal alignment of the two sequences. The percentage may be calculated as follows: by determining the number of positions at which either the identical nucleic acid base or amino acid residue occurs in both sequences or a nucleic acid base or amino acid residue to yield the number of matched positions, dividing the number of matched positions by the total number of positions in the window of comparison and multiplying the result by 100 to yield the percentage of sequence identity. Optionally, the percentage may be calculated as follows: by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Herein, the "reference sequence" refers to a designated sequence used as a basis for sequence comparison. The reference sequence may be a subset of a larger sequence, for example, a segment of a full-length gene or a polypeptide sequence.

Site-directed mutation: refers to the introduction of a desired change (usually a change that represents a favorable direction) into a target DNA fragment (may be a genome, or a plasmid) by methods such as a polymerase chain reaction (PCR), including addition, deletion, point mutation of bases and the like. The site-directed mutation may rapidly and efficiently improve the characters and representation of a target protein expressed by DNA, and is a very useful means in genetic research work.

A KRED mutant E144A+L152Y+L198Q+E201G+G6S+L146M+147V+D42E+T199V derived from *Acetobacter pasteurianus* 386B (as a template of the present disclosure, it has the amino acid sequence of SEQ ID NO: 1. In the present disclosure, "E144A" is taken as an example, it means "original amino acid+site+mutated amino acid", namely, E in the 144-th site is changed into A) may catalyze a target substrate to obtain a product, but its stability needs to be further improved. The present disclosure seeks to improve the stability of KRED by a method of directed evolution.

```
SEQ ID NO: 1:
MARVASKVAIVSGAANGIGKATAQLLAKEGAKVVIGDLKEE

EGQKAVAEIKAAGGEAAFVKLNVTDEAAWKAAIGQTLKLYG

RLDIAVNNAGIAYSGSVESTSLEDWRRVQSINLDGVFLGTQ

VAIEAMKKSGGGSIVNLSSIAGMVGDPMYAAYNASKGGVRL

FTKSAALHCAKSGYKIRVNSVHPGYIWTPMVAGQVKGDAAA

RQKLVDLHPIGHLGEPNDIAYGILYLASDESKFVTGSELVI

DGGYTAQ
```

In the present application, firstly, a mutation site is introduced into KRED by a mode of the site-directed mutation, the activity of the mutant is detected, and the mutant with the improved activity is selected. Herein the stability of the mutant E144A+L152Y+L198Q+E201G+G6S+L146M+147V+D42E+T199V+K200H is improved by about 3 times compared to a starting template. Subsequently, the mutation is continued with E144A+L152Y+L198Q+E201G+G6S+L146M+147V+D42E+T199V+K200H as a template, in order to obtain a mutant with more significant stability improvement.

The method for introducing the site-directed mutation by using the whole-plasmid PCR is simple and effective, and is a method used more at present. A principle thereof is that after a pair of primers (forward and reverse) containing mutation sites are annealed with a template plasmid, "cyclic extension" is performed by using a polymerase, and the so-called cyclic extension is that the polymerase extends the primer according to the template, is returned to a 5-terminal of the primer and terminated after one circle, and subjected to a cycle of repeatedly heated and annealed extension, this reaction is different from rolling circle amplification, and does not form multiple tandem copies. Extension products of the forward and reverse primers are paired to form an open-circle plasmid with an incision after annealed. A Dpn I enzyme-digested extension product, because the original template plasmid is derived from conventional *Escherichia coli*, is modified by dam methylation, and is sensitive to Dpn I so as to be shredded, but a plasmid with a mutant sequence synthesized in vitro is not cut because it is not methylated, so it may be successfully transformed in subsequent transformation, and a clone of a mutant plasmid may be obtained. The above mutant plasmid is transformed into an *Escherichia coli* cell, and over-expressed in the *Escherichia coli*. After that, a crude enzyme is obtained through a method of ultrasonic cell-break. An optimum condition of transaminase induced expression is as follows: 25° C., and inducing in 0.1 mM IPTG for 16 h. In a typical embodiment of the present disclosure, a ketoreductase mutant is provided. The ketoreductase mutant has an amino acid sequence obtained by the mutation of the amino acid sequence shown in SEQ ID NO: 1, and the mutation includes a mutation site K200H. In the present disclosure, the mutant obtained by mutation takes a ketone compound as a raw material, the chiral alcohol may be efficiently produced by stereoselective reduction, and the stability is greatly improved, which is suitable for popularization and application to the industrial production of the chiral alcohol.

Preferably, the mutation includes at least one of the following mutation sites: A15, K28, G36, K39, G43, Q44, A46, V47, F59, K61, T65, K71, A94V, A144, M146, Y152, N156, I86, K208 or K237; or the amino acid sequence of the ketoreductase mutant is an amino acid sequence having the mutation site in a mutated amino acid sequence, and having more than 95% identity with the mutated amino acid sequence. The above mutation sites may further improve the stability of the enzyme. Preferably, the mutation include at least one of the following mutation sites: A15C, K28A/E/M/Q/R/S, G36C, K39I/V, G43C/M, Q44R, A46C, V47C, F59C, K61E/H, T65A, K71R, A94V, A144T, M146I, Y152F, N156S, I86V, K208R or K237E. Herein, "/" represents "or".

In a typical embodiment of the present disclosure, the mutation includes any one of the following mutation site combinations: Q44R+N156S+K200H+G201D, Q44R+N156S+K200H+G201D+M146I+K61H+K208R+A94V+K39I, Q44R+N156S+K200H Q44R+N156S+K200H+G201D, Q44R+N156S+K200H+G201D+M146I, Q44R+N156S+K200H+G201D+M146I+K61H, Q44R+N156S+K200H+G201D+M146I+K61H+I86V Q44R+N156S+K200H+G201D+M146I+K61H+K208R Q44R+N156S+K200H+G201D+M146I+K61H+K208R+A94V Q44R+N156S+K200H+G201D+M146I+K61H+K208R+A94V+K39I+A15C, Q44R+N156S+K200H+G201D+M146I+K61H+K208R+A94V+K39I+A15C+A46C, Q44R+N156S+K200H+G201D+M146I+K61H+K208R+A94V+K39I, or Q44R+N156S+K200H+G201D+M146I+K61H+K208R+A94V+K39I+A15C+A46C+G43M.

More preferably, the occurrence of the amino acid mutation includes any one of the following mutation site combinations: I86V+M146I+K200H, M146I+K200H, M146L+N156S+K200H, M146L+K200H, K200H+G201D, Q44R+M146I+K200H, K61E+K200H+K237E, 186V+M146I+K200H, M146I+K200H+G201D, M146L+K200H+G201 D, N156S+K200H+G201 D, K200H+G201D+K237E, K28E+M146I+K200H+G201D, K28E+M146L+K200H+G201D, K28E+N156S+K200H+G201D, Q44R+M146L+K200H+G201D, Q44R+N156S+K200H+G201D, 186V+M146I+K200H+K61H, I86V+M146I+K200H+K208R, I86V+M146I+K200H+G201D, 186V+M146L+K200H+G201D, Q44R+N156S+K200H+G201 D, Q44R+N156S+K200H+G201D+M146I, Q44R+N156S+K200H+G201D+M146I+K61H, Q44R+N156S+K200H+G201D+M146I+K61H+K28E, Q44R+N156S+K200H+G201D+M146I+K61H+T65A, Q44R+N156S+K200H+G201D+M146I+K61H+I86V, Q44R+N156S+K200H+G201D+M146I+K61H+K208R, Q44R+N156S+K200H+G201D+M146I+K61H+I86V+K28E, Q44R+N156S+K200H+G201D+M146I+K61H+I86V+K39I, Q44R+N156S+K200H+G201D+M146I+K61H+I86V+T65A, Q44R+N156S+K200H+G201D+M146I+K61H+I86V+A94V, Q44R+N156S+K200H+G201D+M146I+K61H+I86V+K208R, Q44R+N156S+K200H+G201D+M146I+K61H+K208R+K28E, Q44R+N156S+K200H+G201D+M146I+K61H+K208R+K39I, Q44R+N156S+K200H+G201D+M146I+K61H+K208R+A94V, Q44R+N156S+K200H+G201D+M146I+K61H+K208R+A94V+K28E, Q44R+N156S+K200H+G201D+M146I+K61H+K208R+A94V+K39I, Q44R+N156S+K200H+G201D+M146I+K61H+K208R+A94V+T65A, Q44R+N156S+K200H+G201D+M146I+K61H+K208R+A94V+K39I+K28E, Q44R+N156S+K200H+G201D+M146I+K61H+K208R+A94V+K39I, Q44R+N156S+K200H+G201D+M146I+K61H+K208R+A94V+K39I+A15C+A46C, Q44R+N156S+K200H+G201D+M146I+K61H+K208R+A94V+K39I+V47C+F59C, Q44R+N156S+K200H+G201D+M146I+K61H+K208R+A94V+K39I+G43C, Q44R+N156S+K200H+G201D+M146I+K61H+K208R+A94V+K39I+A15C+A46C+K28E, Q44R+N156S+K200H+G201D+M146I+K61H+K208R+A94V+K39I+A15C+A46C+K28R, Q44R+N156S+K200H+G201D+M146I+K61H+K208R+A94V+K39I+A15C+A46C+K28Q, Q44R+N156S+K200H+G201D+M146I+K61H+K208R+A94V+K39I+A15C+A46C+K28M, Q44R+N156S+K200H+G201D+M146I+K61H+K208R+A94V+K39I+A15C+A46C+K28A, Q44R+N156S+K200H+G201D+M146I+K61H+K208R+A94V+K39I+A15C+A46C+K28S, Q44R+N156S+K200H+G201D+M146I+K61H+K208R+A94V+K39I+A15C+A46C+G43M, Q44R+N156S+K200H+G201D+M146I+K61H+K208R+A94V+K39I+A15C+A46C+I86V, Q44R+N156S+K200H+G201D+M146I+K61H+K208R+A94V+K39I+A15C+A46C+G43M, Q44R+N156S+K200H+G201D+M146I+K61H+K208R+A94V+K39I+A15C+A46C+G43M+G36C, Q44R+N156S+K200H+G201D+M146I+K61H+K208R+A94V+K39I+A15C+A46C+G43M+139V, Q44R+N156S+K200H+G201D+M146I+K61H+K208R+A94V+K39I+A15C+A46C+G43M+K71R, Q44R+N156S+K200H+G201D+M146I+K61H+K208R+A94V+K39I+A15C+A46C+G43M+A144T, Q44R+N156S+K200H+G201D+M146I+K61H+K208R+A94V+K39I+A15C+A46C+G43M+Y152F, Q44R+N156S+K200H+G201D+M146I+K61H+K208R+A94V+K39I+A15C+A46C+G43M+K28E or Q44R+N156S+K200H+G201D+M146I+K61H+K208R+A94V+K39I+A15C+A46C+G43M+G36C.

According to a typical embodiment of the present disclosure, a DNA molecule is provided. The DNA molecule encodes the above ketoreductase mutant. The above ketoreductase encoded by the DNA molecule has the good activity.

The above DNA molecule of the disclosure may also exist in the form of an "expression cassette". The "expression cassette" refers to a linear or circular nucleic acid molecule that encompasses DNA and RNA sequences capable of guiding expression of a specific nucleotide sequence in an appropriate host cell. Generally, including a promoter which is effectively linked with a target nucleotide, it is optionally effectively linked with a termination signal and/or other control elements. The expression cassette may also include a sequence required for proper translation of the nucleotide sequence. A coding region usually encodes a target protein, but also encodes a target function RNA in a sense or antisense direction, for example an antisense RNA or an untranslated RNA. The expression cassette including a target polynucleotide sequence may be chimeric, which means that at least one of components thereof is heterologous to at least one of the other components thereof. The expression cassette may also be existent naturally, but obtained with effective recombinant formation for heterologous expression. According to a typical embodiment of the present disclosure, a recombinant plasmid is provided. The recombinant plasmid contains any one of the above DNA molecules. The DNA molecule in the above recombinant plasmid is placed in an appropriate position of the recombinant plasmid, so that the above DNA molecule may be correctly and smoothly replicated, transcribed or expressed.

Although a qualifier used in the disclosure while the above DNA molecule is defined is "contain", it does not mean that other sequences which are not related to a function thereof may be arbitrarily added to both ends of the DNA sequence. Those skilled in the art know that in order to meet the requirements of recombination operations, it is necessary to add suitable enzyme digestion sites of a restriction enzyme at two ends of the DNA sequence, or additionally increase a start codon, a termination codon and the like, therefore, if the closed expression is used for defining, these situations may not be covered truly.

A term "plasmid" used in the present disclosure includes any plasmid, cosmid, bacteriophage or agrobacterium binary nucleic acid molecule in double-stranded or single-stranded linear or circular form, preferably a recombinant expression plasmid, which may be a prokaryotic expression plasmid or may be a eukaryotic expression plasmid, preferably the prokaryotic expression plasmid, in some embodiments, the recombinant plasmid is selected from pET-22a (+), pET-22b (+) pET-3a (+), pET-3d (+), pET-11a (+), pET-12a (+), pET-14b (+) pET-15b (+) pET-16b (+) pET-17b (+), pET-19b (+), pET-20b (+) pET-21a (+), pET-23a (+), pET-23b (+), pET-24a (+) pET-25b (+), pET-26b (+) pET-27b (+) pET-28a (+) pET-29a (+) pET-30a (+), pET-31b (+) pET-32a (+), pET-35b (+) pET-38b (+) pET-39b (+), pET-40b (+), pET-41a (+), pET-41b (+) pET-42a (+), pET-43a (+) pET-43b (+) pET-44a (+), pET-49b (+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19. More preferably, the above recombinant plasmid is pET-22b (+).

According to a typical embodiment of the present disclosure, a host cell is provided, and the host cell contains any one of the above recombinant plasmids. The host cell suitable for the present disclosure includes, but is not limited to, a prokaryotic cell, yeast or a eukaryotic cell. Preferably the prokaryotic cell is eubacteria, for example Gram-negative bacteria or Gram-positive bacteria. More preferably, the prokaryotic cell is an *Escherichia coli* BL21 cell or an *Escherichia coli* DH5a competent cell.

According to a typical embodiment of the present disclosure, a method for producing a chiral alcohol is provided. The method includes a step of catalyzing a reduction reaction of a latent chiral ketone compound to produce the chiral alcohol by a ketoreductase, and the ketoreductase is any one of the above ketoreductase mutants. Since the ketoreductase mutant of the present disclosure has the good activity characteristics, the chiral alcohol prepared by using the ketoreductase mutant of the present disclosure may increase the reaction rate, improve the substrate concentration, reduce the amount of the enzyme, and reduce the difficulty of post-treatment.

In the present disclosure, the chiral ketone compound includes, but is not limited to, those with the following structural formula

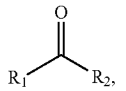

herein $R_1$ and $R_2$ are each independently an alkyl, a cycloalkyl, an aryl or a heteroaryl, or $R_1$ and $R_2$ form a heterocyclyl, a carbocyclyl or a heteroaryl together with carbon in a carbonyl, heteroatom in the heterocyclyl or the heteroaryl is each independently at least one of nitrogen, oxygen or sulfur, an aryl group in the aryl, a heteroaryl group in the heteroaryl, a carbocyclyl group in the carbocyclyl or a heterocyclyl group in the heterocyclyl is each independently unsubstituted or substituted with at least one of a halogen, an alkoxy, or an alkyl; and preferably, $R_1$ and $R_2$ are each independently a $C_1$-$C_8$ alkyl, a $C_5$-$C_{10}$ cycloalkyl, a $C_5$-$C_{10}$ aryl or a $C_5$-$C_{10}$ heteroaryl, or $R_1$ and $R_2$ form a $C_5$-$C_{10}$ heterocyclyl, a $C_5$-$C_{10}$ carbocyclyl or a $C_5$-$C_{10}$ heteroaryl together with carbon in a carbonyl, heteroatoms in the $C_5$-$C_{10}$ heterocyclyl and the $C_5$-$C_{10}$ heteroaryl are each independently at least one of nitrogen, oxygen or sulfur, an aryl group in the $C_5$-$C_{10}$ aryl, a heteroaryl group in the $C_5$-$C_{10}$ heteroaryl, a carbocyclyl group in the $C_5$-$C_{10}$ carbocyclyl or a heterocyclyl group in the $C_5$-$C_{10}$ heterocyclyl is each independently unsubstituted or substituted with at least one of a halogen, an alkoxy, or an alkyl.

Preferably, the structure of the ketone compound is

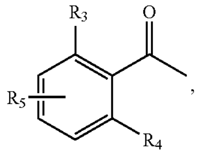

herein, $R_3$ is H, F, Cl, Br or $CH_3$, $R_4$ is H, F, Cl, Br or $CH_3$, and $R_5$ is H, F, Cl, Br, $CH_3$, $OCH_3$ or $CH_2CH_3$.

More preferably, the ketone compound is

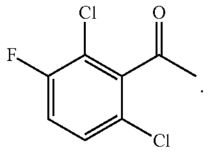

The host cell previously described in the present disclosure may be used for the expression and isolation of the ketoreductase, or optionally, they may be used directly to convert a ketone substrate into a chiral alcohol product. Preferably, the prokaryotic cell is *Escherichia coli*.

The reduction reaction described above generally requires a cofactor, it is typically NADH or NADPH, and the reduction reaction may include a system for regenerating the cofactor, for example D-glucose, coenzyme $NAD^+$, and glucose dehydrogenase GDH; a formate compound, coenzyme $NAD^+$ and formate dehydrogenase FDH; or isopropanol, coenzyme $NAD^+$ and alcohol dehydrogenase ADH. In some embodiments using the purified ketoreductases, such cofactors and optionally such cofactor regeneration systems may be usually added to a reaction medium with the substrate and the ketoreductase. Similar to the ketoreductase, any enzymes including the cofactor regeneration system may be in the form of an extract or a lysate of such cells, or added to a reaction mixture as a purified enzyme. In embodiments using the cell extract or the cell lysate, the cell used to produce the extract or the lysate may be an enzyme expressed that only contains the cofactor regeneration system or contains the cofactor regeneration system and the ketoreductase. In embodiments using a whole cell, the cell may be an enzyme expressed that contains the cofactor regeneration system and the ketoreductase.

Whether the whole cell, the cell extract, or the purified ketoreductase is used, a single ketoreductase may be used, or optionally, a mixture of two or more ketoreductases may be used.

The reaction system for producing the chiral alcohol by catalyzing the reduction reaction on the chiral ketone compound by the ketoreductase further includes a coenzyme, a coenzyme regeneration system and a buffer.

Due to the higher catalytic activity of the ketoreductase mutant of the present disclosure, the concentration of the substrate may be increased, the production efficiency may be improved, and the concentration of the chiral ketone compound in the reaction system is 1 g/L-200 g/L.

The pH value of the reaction system is 5-9, and the reaction temperature of the reaction system is 4-60° C.; and the buffer is a phosphate buffer, a Tris-hydrochloric acid buffer, a sodium barbital-hydrochloric acid buffer or a citric acid-sodium citrate buffer.

The beneficial effects of the present disclosure are further described below in combination with the embodiments.

In the present application, an enzyme activity detection method is as follows:

1. Reagent Preparation:

Substrate (R)-1-(2,4-dichloroacetophenone) mother solution 60 mM: 56.7 mg substrate is weighed and dissolved in 5 mL of 0.1 M phosphate buffer (PB) with pH 7.0, and it is placed in a water bath kettle at 50° C. for dissolving.

NADH mother solution 10 mM: 33.17 mg NADH is weighed and dissolved in 5 mL of 0.1 M PB with pH 7.0.

2. Enzyme Activity System:

The enzyme is firstly added, then a mixture of the substrate (R)-1-(2,4-dichloroacetophenone) NADH and Buffer is added, it is placed in a microplate reader, and the enzyme activity is detected at 30° C. and 340 nm wavelength.

A detection system is shown in Table 1.

TABLE 1

| System | Addition amount | Final concentration |
|---|---|---|
| Enzyme mutant | 20 μL | N/A |
| Substrate | 50 μL | 10 mM |
| NADH | 10 μL | 0.33 mM |
| 0.1M PB pH 7.0 buffer | 220 μL | N/A |

The stability is expressed as the residual activity, namely the percentage value of the activity after the treatment to the activity before the treatment.

The KRED mutant E144A+L152Y+L198Q+E201G+G6S+L146M+147V+D42E+T199V is referred to as a "template" in the present disclosure, and the listed mutation sites are mutations performed on the basis of the "template".

Embodiment 1

The "template" and the mutant are incubated at 45° C. and 53° C. for 1 h respectively, and then the activities thereof are measured. Compared with those without incubation, the stability is expressed as a percentage of its residual activity and initial activity. The thermal stability of all mutants is measured at 53° C. and results are shown in Table 2.

TABLE 2

| Mutant | Stability (%) |
|---|---|
| Template | +++ (45° C.) |
| Template | + (53° C.) |
| K200H | ++ |
| I86V + M146I + K200H | +++ |
| M146I + K200H | +++ |
| M146L + N156S + K200H | ++++ |
| M146L + K200H | +++ |
| K200H + G201D | +++ |
| Q44R + M146I + K200H | +++ |
| K61E + K200H + K237E | ++ |
| I86V + M146I + K200H | +++ |
| M146I + K200H + G201D | ++++ |
| M146L + K200H + G201D | +++ |
| N156S + K200H + G201D | ++++ |
| K200H + G201D + K237E | +++ |
| K28E + M146I + K200H + G201D | ++++ |
| K28E + M146L + K200H + G201D | +++ |
| K28E + N156S + K200H + G201D | ++++ |
| Q44R + M146L + K200H + G201D | +++ |
| Q44R + N156S + K200H + G201D | ++++ |
| I86V + M146I + K200H + K61H | ++++ |
| I86V + M146I + K200H + K208R | ++++ |
| I86V + M146I + K200H + G201D | +++ |
| I86V + M146L + K200H + G201D | +++ |

+ represents the stability, + represents residual activity 0-5%,
++ represents residual activity 5-10%,
+++ represents residual activity 10-50%, and
++++ represents residual activity 50-95%.

Embodiment 2

Combining saturation mutations may obtain a mutant with a synergistic effect among several mutation sites, and may optimize the composition of an amino acid thereof. Q44R+N156S+K200H+G201D is taken as a template, the mutation site combination is performed. At this time, the enzyme solution treatment condition is that it is treated at 65° C. for 1 h, and then the activity thereof is measured. Compared with those without incubation, the stability is expressed as a percentage of its residual activity and initial activity.

Preparation method of enzyme solution in high-throughput screening: a 96-well plate is centrifuged to remove a supernatant medium, and 200 μL of enzymatic solution (lysozyme 2 mg/mL, polymyxin 0.5 mg/mL, and pH=7.0) is added to each well, it is incubated at 37° C. and crushed for 3 h. Enzyme activity detection method: an enzyme is firstly added, then a mixture of substrate (R)-1-(2,4-dichloroaceto-phenone), NADH and Buffer is added, it is placed in a microplate reader, the enzyme activity is detected at 30° C. and 340 nm wavelength, and results are shown in Table 3.

TABLE 3

| Mutant | Stability (%) |
|---|---|
| Q44R + N156S + K200H + G201D | + |
| Q44R + N156S + K200H + G201D + M146I | ++ |
| Q44R + N156S + K200H + G201D + M146I + K61H | +++ |
| Q44R + N156S + K200H + G201D + M146I + K61H + K28E | ++++ |
| Q44R + N156S + K200H + G201D + M146I + K61H + T65A | +++ |
| Q44R + N156S + K200H + G201D + M146I + K61H + I86V | +++ |
| Q44R + N156S + K200H + G201D + M146I + K61H + K208R | ++++ |
| Q44R + N156S + K200H + G201D + M146I + K61H + I86V + K28E | +++ |
| Q44R + N156S + K200H + G201D + M146I + K61H + I86V + K39I | +++ |
| Q44R + N156S + K200H + G201D + M146I + K61H + I86V + T65A | ++ |
| Q44R + N156S + K200H + G201D + M146I + K61H + I86V + A94V | ++++ |
| Q44R + N156S + K200H + G201D + M146I + K61H + I86V + K208R | +++ |
| Q44R + N156S + K200H + G201D + M146I + K61H + K208R + K28E | ++++ |
| Q44R + N156S + K200H + G201D + M146I + K61H + K208R + K39I | ++++ |
| Q44R + N156S + K200H + G201D + M146I + K61H + K208R + A94V | ++++ |
| Q44R + N156S + K200H + G201D + M146I + K61H + K208R + A94V + K28E | ++++ |
| Q44R + N156S + K200H + G201D + M146I + K61H + K208R + A94V + K39I | ++++ |
| Q44R + N156S + K200H + G201D + M146I + K61H + K208R + A94V + T65A | ++++ |
| Q44R + N156S + K200H + G201D + M146I + K61H + K208R + A94V + K39I + K28E | ++++ |

+ represents the stability,
+ represents residual activity 0-5%,
++ represents residual activity 5-10%,
+++ represents residual activity 10-50%, and
++++ represents residual activity 50-95%.

Embodiment 3

The mutation is continued with Q44R+N156S+K200H+G201D+M146I+K61H+K208R+A94V+K39I as a template. At this time, the enzyme solution treatment condition is that it is treated at 71° C. for 1 h, and then the activity thereof is measured. Compared with those without incubation, the stability is expressed as a percentage of its residual activity and initial activity.

Preparation method of enzyme solution in high-throughput screening: a 96-well plate is centrifuged to remove a supernatant medium, and 200 μL of enzymatic solution (lysozyme 2 mg/mL, polymyxin 0.5 mg/mL, and pH=7.0) is added to each well, it is incubated at 37° C. and crushed for 3 h. Enzyme activity detection method: an enzyme is firstly added, then a mixture of substrate (R)-1-(2,4-dichloroaceto-phenone), NADH and Buffer is added, it is placed in a microplate reader, the enzyme activity is detected at 30° C. and 340 nm wavelength, and results are shown in Table 4.

TABLE 4

| Mutant | Stability (%) |
|---|---|
| Q44R + N156S + K200H + G201D + M146I + K61H + K208R + A94V + K39I | + |
| Q44R + N156S + K200H + G201D + M146I + K61H + K208R + A94V + K39I + A15C + A46C | ++ |
| Q44R + N156S + K200H + G201D + M146I + K61H + K208R + A94V + K39I + V47C + F59C | ++ |
| Q44R + N156S + K200H + G201D + M146I + K61H + K208R + A94V + K39I + G43C | ++ |
| Q44R + N156S + K200H + G201D + M146I + K61H + K208R + A94V + K39I + A15C + A46C + K28E | +++ |
| Q44R + N156S + K200H + G201D + M146I + K61H + K208R + A94V + K39I + A15C + A46C + K28R | ++ |
| Q44R + N156S + K200H + G201D + M146I + K61H + K208R + A94V + K39I + A15C + A46C + K28Q | +++ |
| Q44R + N156S + K200H + G201D + M146I + K61H + K208R + A94V + K39I + A15C + A46C + K28M | +++ |
| Q44R + N156S + K200H + G201D + M146I + K61H + K208R + A94V + K39I + A15C + A46C + K28A | ++ |
| Q44R + N156S + K200H + G201D + M146I + K61H + K208R + A94V + K39I + A15C + A46C + K28S | ++ |
| Q44R + N156S + K200H + G201D + M146I + K61H + K208R + A94V + K39I + A15C + A46C + G43M | ++++ |
| Q44R + N156S + K200H + G201D + M146I + K61H + K208R + A94V + K39I + A15C + A46C + I86V | ++ |
| Q44R + N156S + K200H + G201D + M146I + K61H + K208R + A94V + K39I + A15C + A46C + G43M | +++ |
| Q44R + N156S + K200H + G201D + M146I + K61H + K208R + A94V + K39I + A15C + A46C + G43M + G36C | ++++ |
| Q44R + N156S + K200H + G201D + M146I + K61H + K208R + A94V + K39I + A15C + A46C + G43M + 139V | +++ |
| Q44R + N156S + K200H + G201D + M146I + K61H + K208R + A94V + K39I + A15C + A46C + G43M + K71R | +++ |
| Q44R + N156S + K200H + G201D + M146I + K61H + K208R + A94V + K39I + A15C + A46C + G43M + A144T | ++ |
| Q44R + N156S + K200H + G201D + M146I + K61H + K208R + A94V + K39I + A15C + A46C + G43M + Y152F | +++ |
| Q44R + N156S + K200H + G201D + M146I + K61H + K208R + A94V + K39I + A15C + A46C + G43M + K28E | ++++ |
| Q44R + N156S + K200H + G201D + M146I + K61H + K208R + A94V + K39I + A15C + A46C + G43M + G36C | ++++ |

+ represents the stability,
+ represents residual activity 0-5%,
++ represents residual activity 5-10%,
+++ represents residual activity 10-50%, and
++++ represents residual activity 50-95%.

Embodiment 4

In the process of improving the stability of an enzyme, the overall rigidity of the enzyme is improved, so a mutant with the improved stability also shows the improved tolerance to chemicals such as glutaraldehyde and organic solvents such as methanol. This is also the extrinsic manifestation of the improved overall rigidity of the mutant.

The previously described mutant is tested for the glutaraldehyde tolerance and the methanol tolerance. Herein the glutaraldehyde tolerance is tested by incubating with 1% glutaraldehyde for 1 h, and then measuring the residual activity, and the glutaraldehyde tolerance is expressed as a percentage of the activity without incubation and the activity with incubation. The methanol tolerance is tested by incubating with 60% methanol solution for 1 h, and then measuring the residual activity, and the methanol tolerance is expressed as a percentage of the activity without incubation and the activity with incubation. Results are shown in Table 5.

TABLE 5

| Mutant | Glutaraldehyde tolerance (%) | Methanol tolerance (%) |
|---|---|---|
| Template | * | # |
| K200H | ** | ## |
| I86V + M146I + K200H | ** | ## |
| M146L + K200H | ** | ## |
| M146L + N156S + K200H | ** | ## |
| K200H + G201D | ** | ## |
| Q44R + M146I + K200H | ** | ## |
| K61E + K200H + K237E | ** | ## |
| I86V + M146I + K200H | ** | ## |
| M146I + K200H + G201D | ** | ## |
| M146L + K200H + G201D | ** | ## |
| N156S + K200H + G201D | ** | ## |
| K200H + G201D + K237E | ** | ## |
| K28E + M146I + K200H + G201D | ** | ## |
| K28E + M146L + K200H + G201D | ** | ## |
| K28E + N156S + K200H + G201D | *** | ### |
| Q44R + M146L + K200H + G201D | ** | ## |
| Q44R + N156S + K200H + G201D | ** | ## |
| I86V + M146I + K200H + K61H | ** | ## |
| I86V + M146I + K200H + K208R | ** | ## |
| I86V + M146I + K200H + G201D | ** | ## |
| I86V + M146L + K200H + G201D | ** | ## |
| Q44R + N156S + K200H + G201D + M146I | *** | ### |
| Q44R + N156S + K200H + G201D + M146I + K61H | ** | ## |
| Q44R + N156S + K200H + G201D + M146I + K61H + K28E | *** | ### |
| Q44R + N156S + K200H + G201D + M146I + K61H + T65A | ** | ## |
| Q44R + N156S + K200H + G201D + M146I + K61H + I86V | *** | ### |
| Q44R + N156S + K200H + G201D + M146I + K61H + I86V + K28E | *** | ### |
| Q44R + N156S + K200H + G201D + M146I + K61H + I86V + K39I | *** | ### |
| Q44R + N156S + K200H + G201D + M146I + K61H + I86V + T65A | *** | ### |
| Q44R + N156S + K200H + G201D + M146I + K61H + I86V + A94V | *** | ### |
| Q44R + N156S + K200H + G201D + M146I + K61H + I86V + K208R | *** | ### |
| Q44R + N156S + K200H + G201D + M146I + K61H + K208R + A94V | *** | ### |
| Q44R + N156S + K200H + G201D + M146I + K61H + K208R + A94V + K28E | *** | ### |
| Q44R + N156S + K200H + G201D + M146I + K61H + K208R + A94V + K39I | *** | ### |
| Q44R + N156S + K200H + G201D + M146I + K61H + K208R + A94V + T65A | *** | ### |
| Q44R + N156S + K200H + G201D + M146I + K61H + K208R + A94V + K39I + K28E | *** | ### |
| Q44R + N156S + K200H + G201D + M146I + K61H + K208R + A94V + K39I | *** | ### |
| Q44R + N156S + K200H + G201D + M146I + K61H + K208R + A94V + K39I + A15C + A46C | **** | #### |
| Q44R + N156S + K200H + G201D + M146I + K61H + K208R + A94V + K39I + V47C + F59C | **** | #### |
| Q44R + N156S + K200H + G201D + M146I + K61H + K208R + A94V + K39I + G43C | *** | ### |
| Q44R + N156S + K200H + G201D + M146I + K61H + K208R + A94V + K39I + A15C + A46C + K28E | **** | #### |
| Q44R + N156S + K200H + G201D + M146I + K61H + K208R + A94V + K39I + A15C + A46C + K28R | **** | #### |

TABLE 5-continued

| Mutant | Glutaraldehyde tolerance (%) | Methanol tolerance (%) |
|---|---|---|
| Q44R + N156S + K200H + G201D + M146I + K61H + K208R + A94V + K39I + A15C + A46C + K28Q | **** | #### |
| Q44R + N156S + K200H + G201D + M146I + K61H + K208R + A94V + K39I + A15C + A46C + K28M | **** | #### |
| Q44R + N156S + K200H + G201D + M146I + K61H + K208R + A94V + K39I + A15C + A46C + K28A | **** | #### |
| Q44R + N156S + K200H + G201D + M146I + K61H + K208R + A94V + K39I + A15C + A46C + G43M | **** | #### |
| Q44R + N156S + K200H + G201D + M146I + K61H + K208R + A94V + K39I + A15C + A46C + I86V | **** | #### |
| Q44R + N156S + K200H + G201D + M146I + K61H + K208R + A94V + K39I + A15C + A46C + G43M | **** | #### |
| Q44R + N156S + K200H + G201D + M146I + K61H + K208R + A94V + K39I + A15C + A46C + G43M + G36C | **** | #### |
| Q44R + N156S + K200H + G201D + M146I + K61H + K208R + A94V + K39I + A15C + A46C + G43M + I39V | **** | #### |
| Q44R + N156S + K200H + G201D + M146I + K61H + K208R + A94V + K39I + A15C + A46C + G43M + K71R | **** | #### |
| Q44R + N156S + K200H + G201D + M146I + K61H + K208R + A94V + K39I + A15C + A46C + G43M + A144T | **** | #### |
| Q44R + N156S + K200H + G201D + M146I + K61H + K208R + A94V + K39I + A15C + A46C + G43M + Y152F | **** | #### |
| Q44R + N156S + K200H + G201D + M146I + K61H + K208R + A94V + K39I + A15C + A46C + G43M + K28E | **** | #### |
| Q44R + N156S + K200H + G201D + M146I + K61H + K208R + A94V + K39I + A15C + A46C + G43M + G36C | **** | #### |

* represents the glutaraldehyde tolerance,
* represents residual activity 0-5%,
** represents residual activity 5-10%,
*** represents residual activity 10-50%, and
**** represents residual activity 50-95%.
# represents the methanol tolerance,
# represents residual activity 0-5%,
## represents residual activity 5-10%,
### represents residual activity 10-50%, and
#### represents residual activity 50-95%.

Embodiment 5

A mutant Q44R+N156S+K200H+G201D+M146I+K61H+K208R+A94V+K39I+A15C+A46C+G43M+G36C is used to verify reactions of different substrates, and results are shown in Table 6.

1) 2 g substrate 2-chloroacetophenone is added to a 25 mL reaction flask, and 0.1 M PB pH7.0, 2 g isopropanol, 20 mg NAD+, and 0.05 g a ketoreductase mutant are added, and mixed uniformly, the total volume is 10 mL, it is placed in a 200 rpm shaker at 50° C., and reacted for 16 hours.

2) 2 g substrate 3-fluoroacetophenone is added to a 25 mL reaction flask, and 0.1 M of PB pH7.0, 2 g isopropanol, 20 mg NAD+, and 0.05 g a ketoreductase mutant are added, and mixed uniformly, the total volume is 10 mL, it is placed in a 200 rpm shaker at 50° C., and reacted for 16 hours.
3) 2 g substrate 4-methoxyacetophenone is added to a 25 mL reaction flask, and 0.1 M of PB pH7.0, 2 g isopropanol, 20 mg NAD+, and 0.05 g a ketoreductase mutant are added, and mixed uniformly, the total volume is 10 mL, it is placed in a 200 rpm shaker at 50° C., and reacted for 16 hours.
4) 2 g substrate ethyl acetoacetate is added to a 25 mL reaction flask, and 0.1 M of PB pH7.0, 2 g isopropanol, 20 mg NAD+, and 0.05 g a ketoreductase mutant are added, and mixed uniformly, the total volume is 10 mL, it is placed in a 200 rpm shaker at 50° C., and reacted for 16 hours.

TABLE 6

| Number | Substrate | Conversion rate (%) | ee |
|---|---|---|---|
| 1 | 2-chloroacetophenone | 99 | >99% |
| 2 | 3-fluoroacetophenone | 99 | >99% |
| 3 | 4-methoxyacetophenone | 99 | >99% |
| 4 | Ethyl acetoacetate | 99 | >99% |

The above are only preferred embodiments of the present disclosure, and are not intended to limit the present disclosure. For those skilled in the art, the present disclosure may have various modifications and changes. Any modifications, equivalent replacements, improvements and the like made within the spirit and principle of the present disclosure shall be included within a scope of protection of the present disclosure.

The invention claimed is:

1. A ketoreductase mutant having the amino acid sequence of SEQ ID NO: 1, with the exception of the mutation site K200H.

2. The ketoreductase mutant according to claim 1, wherein the mutation also comprises at least one of the following mutation sites: A15, K28, G36, K39, G43, Q44, A46, V47, F59, K61, T65, K71, A94V, A144, M146, Y152, N156, I86, K208 or K237.

3. The ketoreductase mutant according to claim 2, wherein the mutation also comprises at least one of the following mutation sites: A15C, K28A/E/M/Q/R/S, G36C, K39I/V, G43C/M, Q44R, A46C, V47C, F59C, K61E/H, T65A, K71R, A94V, A144T, M146I, Y152F, N156S, I86V, K208R or K237E.

4. The ketoreductase mutant according to claim 3, wherein the mutation comprises any one of the following mutation site combinations: Q44R+N156S+K200H, Q44R+N156S+K200H+G201D, Q44R+N156S+K200H+G201D+M146I, Q44R+N156S+K200H+G201D+M146I+K61H, Q44R+N156S+K200H+G201D+M146I+K61H+I86V, Q44R+N156S+K200H+G201D+M146I+K61H+K208R, Q44R+N156S+K200H+G201D+M146I+K61H+K208R+A94V, Q44R+N156S+K200H+G201D+M146I+K61H+K208R+A94V+K39I+A15C, Q44R+N156S+K200H+G201D+M146I+K61H+K208R+A94V+K39I+A15C+A46C, Q44R+N156S+K200H+G201D+M146I+K61H+K208R+A94V+K39I, or

Q44R+N156S+K200H+G201D+M146I+K61H+K208R+A94V+K39I+A15C+A46C+G4 3M.

5. The ketoreductase mutant according to claim 1, wherein the occurrence of the amino acid mutation comprises any one of the following mutation site combinations: I86V+M146I+K200H, M146I+K200H, M146L+N156S+K200H, M146L+K200H, K200H+G201D, Q44R+M146I+K200H, K61E+K200H+K237E, I86V+M146I+K200H, M146I+K200H+G201D, M146L+K200H+G201D, N156S+K200H+G201D, K200H+G201D+K237E, K28E+M146I+K200H+G201D, K28E+M146L+K200H+G201D, K28E+N156S+K200H+G201D, Q44R+M146L+K200H+G201D, Q44R+N156S+K200H+G201D, I86V+M146I+K200H+K61H, I86V+M146I+K200H+K208R, I86V+M146I+K200H+G201D, I86V+M146L+K200H+G201D, Q44R+N156S+K200H+G201D, Q44R+N156S+K200H+G201D+M146I, Q44R+N156S+K200H+G201D+M146I+K61H, Q44R+N156S+K200H+G201D+M146I+K61H+K28E, Q44R+N156S+K200H+G201D+M146I+K61H+T65A, Q44R+N156S+K200H+G201D+M146I+K61H+I86V, Q44R+N156S+K200H+G201D+M146I+K61H+K208R, Q44R+N156S+K200H+G201D+M146I+K61H+I86V+K28E, Q44R+N156S+K200H+G201D+M146I+K61H+I86V+K39I, Q44R+N156S+K200H+G201D+M146I+K61H+I86V+T65A, Q44R+N156S+K200H+G201D+M146I+K61H+I86V+A94V, Q44R+N156S+K200H+G201D+M146I+K61H+I86V+K208R, Q44R+N156S+K200H+G201D+M146I+K61H+K208R+K28E, Q44R+N156S+K200H+G201D+M146I+K61H+K208R+K39I, Q44R+N156S+K200H+G201D+M146I+K61H+K208R+A94V, Q44R+N156S+K200H+G201D+M146I+K61H+K208R+A94V+K28E, Q44R+N156S+K200H+G201D+M146I+K61H+K208R+A94V+K39I, Q44R+N156S+K200H+G201D+M146I+K61H+K208R+A94V+T65A, Q44R+N156S+K200H+G201D+M146I+K61H+K208R+A94V+K39I+K28E, Q44R+N156S+K200H+G201D+M146I+K61H+K208R+A94V+K39I, Q44R+N156S+K200H+G201D+M146I+K61H+K208R+A94V+K39I+A15C+A46C, Q44R+N156S+K200H+G201D+M146I+K61H+K208R+A94V+K39I+V47C+F59C, Q44R+N156S+K200H+G201D+M146I+K61H+K208R+A94V+K39I+G43C, Q44R+N156S+K200H+G201D+M146I+K61H+K208R+A94V+K39I+A15C+A46C+K28E, Q44R+N156S+K200H+G201D+M146I+K61H+K208R+A94V+K39I+A15C+A46C+K28R, Q44R+N156S+K200H+G201D+M146I+K61H+K208R+A94V+K39I+A15C+A46C+K28Q, Q44R+N156S+K200H+G201D+M146I+K61H+K208R+A94V+K39I+A15C+A46C+K28M, Q44R+N156S+K200H+G201D+M146I+K61H+K208R+A94V+K39I+A15C+A46C+K28A, Q44R+N156S+K200H+G201D+M146I+K61H+K208R+A94V+K39I+A15C+A46C+K28S, Q44R+N156S+K200H+G201D+M146I+K61H+K208R+A94V+K39I+A15C+A46C+G43M, Q44R+N156S+K200H+G201D+M146I+K61H+K208R+A94V+K39I+A15C+A46C+I86V, Q44R+N156S+K200H+G201D+M146I+K61H+K208R+A94V+K39I+A15C+A46C+G43M, Q44R+N156S+K200H+G201D+M146I+K61H+K208R+A94V+K39I+A15C+A46C+G43M+G36C, Q44R+N156S+K200H+G201D+M146I+K61H+K208R+A94V+K39I+A15C+A46C+G43M+I39V, Q44R+N156S+K200H+G201D+M146I+K61H+K208R+A94V+K39I+A15C+A46C+G43M+K71R, Q44R+N156S+K200H+G201D+M146I+K61H+K208R+A94V+K39I+A15C+A46C+G43M+A144T, Q44R+N156S+K200H+G201D+M146I+K61H+K208R+A94V+K39I+A15C+A46C+G43M+Y152F, Q44R+N156S+K200H+G201D+M146I+K61H+K208R+A94V+K39I+A15C+A46C+G43M+K28E, or Q44R+N156S+K200H+G201D+M146I+K61H+K208R+A94V+K39I+A15C+A46C+G43M+G36C.

6. A DNA molecule, wherein the DNA molecule encodes the ketoreductase mutant according to claim 1.

7. A recombinant plasmid, wherein the recombinant plasmid contains the DNA molecule according to claim 6.

8. The recombinant plasmid according to claim 7, wherein the recombinant plasmid is pET-22a (+), pET-22b (+), pET-3a (+), pET-3d (+), pET-11a (+), pET-12a (+), pET-14b (+), pET-15b (+), pET-16b (+), pET-17b (+), pET-19b (+), pET-20b (+), pET-21a (+), pET-23a (+), pET-23b (+), pET-24a (+), pET-25b (+), pET-26b (+), pET-27b (+), pET-28a (+), pET-29a (+), pET-30a (+), pET-31b (+), pET-32a (+), pET-35b (+), pET-38b (+), pET-39b (+), pET-40b (+), pET-41a (+), pET-41b (+), pET-42a (+), pET-43a (+), pET-43b (+), pET-44a (+), pET-49b (+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

9. A host cell, wherein the host cell contains the recombinant plasmid according to claim 7.

10. The host cell according to claim 9, wherein the host cell comprises a prokaryotic cell or a eukaryotic cell.

11. A method for producing a chiral alcohol, comprising a step of catalyzing a reduction reaction of a latent chiral ketone compound to produce the chiral alcohol by a ketoreductase, wherein the ketoreductase is the ketoreductase mutant according to claim 1.

12. The method according to claim 11, wherein the chiral ketone compound has the following structural formula

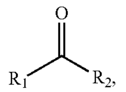

wherein $R_1$ and $R_2$ are each independently an alkyl, a cycloalkyl, an aryl or a heteroaryl, or $R_1$ and $R_2$, together with carbon in a carbonyl, form a heterocyclyl, a carbocyclyl or a heteroaryl, heteroatoms in the heterocyclyl is at least one of nitrogen, oxygen or sulfur, heteroatoms in the heteroaryl is at least one of nitrogen, oxygen or sulfur; and an aryl group in the aryl, a heteroaryl group in the heteroaryl, a carbocyclyl group in the carbocyclyl or a heterocyclyl group in the heterocyclyl is each independently unsubstituted or substituted with at least one of a halogen, an alkoxy, or an alkyl.

13. The method according to claim 11, wherein a reaction system for producing the chiral alcohol by reducing the ketone compound with the ketoreductase further comprises a coenzyme, a coenzyme regeneration system and a buffer.

14. The method according to claim 13, wherein the concentration of the ketone compound in the reaction system is 1 g/L-200 g/L.

15. The method according to claim 13, wherein the pH value of the reaction system is 5-9, and the reaction temperature of the reaction system is 4-60° C.

16. The method according to claim 13, wherein the coenzyme is NADH.

17. The method according to claim 16, wherein the coenzyme regeneration system includes: isopropanol, coenzyme $NAD^+$ and ketoreductase.

18. The method according to claim 13, wherein the buffer is a phosphate buffer, a Tris-hydrochloric acid buffer, a sodium barbital-hydrochloric acid buffer or a citric acid-sodium citrate buffer.

19. The method according to claim 12, wherein the structure of the ketone compound is

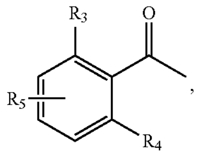

wherein, $R_3$ is H, F, Cl, Br or $CH_3$, $R_4$ is H, F, Cl, Br or $CH_3$, and $R_5$ is H, F, Cl, Br, $CH_3$, $OCH_3$ or $CH_2CH_3$.

20. The method according to claim 12, wherein the ketone compound is

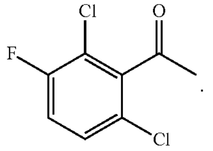

* * * * *

SEQUENCE LISTING

```
<160> NUMBER OF SEQ ID NOS: 1

<210> SEQ ID NO 1
<211> LENGTH: 253
<212> TYPE: PRT
<213> ORGANISM: Acetobacter pasteurianus 386B

<400> SEQUENCE: 1

Met Ala Arg Val Ala Ser Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Glu Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Ala
    130                 135                 140

Gly Met Val Gly Asp Pro Met Tyr Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Gln Val Lys Gly Asp Ala Ala Ala Arg Gln Lys
        195                 200                 205

Leu Val Asp Leu His Pro Ile Gly His Leu Gly Glu Pro Asn Asp Ile
    210                 215                 220
```

-continued

```
Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250
```